(12) United States Patent
Cheng et al.

(10) Patent No.: US 7,579,015 B2
(45) Date of Patent: Aug. 25, 2009

(54) LIQUID COSMETIC CLEANSING-AGENT COMPOSITION

(75) Inventors: Guang Yu Cheng, Neshanic Station, NJ (US); Divyesh Patel, Forest Lakes, MN (US); Domnica Cernasov, Ringwood, NJ (US); Juan R. Mateu, Oak Ridge, NJ (US); Ralph Macchio, Sparta, NJ (US)

(73) Assignee: Coty, B.V., Haarlem (NL)

( * ) Notice: Subject to any disclaimer, the term of this patent is extended or adjusted under 35 U.S.C. 154(b) by 298 days.

(21) Appl. No.: 10/512,498

(22) PCT Filed: Apr. 24, 2003

(86) PCT No.: PCT/EP03/04266

§ 371 (c)(1), (2), (4) Date: Jun. 15, 2005

(87) PCT Pub. No.: WO03/090707

PCT Pub. Date: Nov. 6, 2003

(65) Prior Publication Data

US 2005/0238601 A1   Oct. 27, 2005

(30) Foreign Application Priority Data

Apr. 25, 2002   (DE)  ................  102 19 295

(51) Int. Cl.
*A61K 8/02* (2006.01)
*A61K 47/48* (2006.01)
*A61K 31/765* (2006.01)

(52) U.S. Cl. .................. 424/401; 424/78.17; 424/78.37

(58) Field of Classification Search ................ 424/401, 424/78.17, 78.37
See application file for complete search history.

(56) References Cited

U.S. PATENT DOCUMENTS

| 5,804,173 A | * | 9/1998 | Hutchins et al. | ......... 424/70.16 |
| 5,871,760 A | * | 2/1999 | Doughty et al. | ............. 424/401 |
| 5,888,492 A | * | 3/1999 | Starch | ..................... 424/78.03 |
| 6,211,263 B1 | * | 4/2001 | Cinelli et al. | ............... 523/111 |
| 6,468,551 B1 | * | 10/2002 | Diec et al. | .................. 424/401 |

* cited by examiner

*Primary Examiner*—Raymond J Henley, III
(74) *Attorney, Agent, or Firm*—Novak Druce + Quigg; Gregory A. Nelson; Gregory M. Lefkowitz

(57) ABSTRACT

The invention relates to a new cosmetic cleansing composition with improved skin conditioning and stability properties. Said cleansing composition contains (in % by weight) 5-60% of a surface-active agent, 0.1-10% of a diblock or triblock copolymer or a mixture thereof, 0.1-10% of a saturated liquid oligomer of an unsaturated fatty acid, said oligomer having more than 30 carbon atoms, 0.1-30% of an oil or fat, 10-80% of water, nd has an improved average foam stability ranging between 35 and 60 mm according to the foam stability test.

13 Claims, No Drawings

LIQUID COSMETIC CLEANSING-AGENT COMPOSITION

Cross Reference To Related Application

This application is a national stage of PCT/EP03/04266 filed Apr. 24, 2003, which claims the priority of German Application DE 102 19 295.2 filed Apr. 25, 2002, under the International Convention.

BACKGROUND OF THE INVENTION

1. Field of the Invention

The present invention relates to a new cosmetic cleansing composition with improved skin conditioning and stability properties.

2. Related Art of the Invention

Skin cleansers are known from U.S. Pat. Nos. 5,578,299 and 5,888,492 respectively, which contain a hydrocarbon oil, a non-ionic or anionic surface-active agent soluble therein, a diblock or triblock copolymer and, optionally, a fatty acid ester acting as an emollient.

In addition, emulsifier-free skin cleansers are known which contain hydrogenated styrene/butadiene copolymers along with other emulsion stabilizers such as acrylate polymers, as disclosed in U.S. Pat. No. 5,928,632.

SUMMARY OF THE INVENTION

The object of the invention is to provide a new liquid cosmetic cleansing composition which has a very good cleansing effect as well as special stability properties and enables excellent skin conditioning.

According to the invention, a liquid cosmetic cleansing composition is provided which comprises
- 5 to 60% by weight of a surface-active agent;
- 0.1 to 10% by weight of a diblock or triblock copolymer or a mixture thereof;
- 0.1 to 10% by weight of a saturated liquid oligomer of an unsaturated fatty acid, said oligomer having more than 30 carbon atoms;
- 0.1 to 30% by weight of an oil or fat;
- 10 to 80% by weight of water,
- which cleansing composition has an improved average foam stability ranging between 35 and 60 mm according to the foam stability test.

Anionic, amphoteric, non-ionic or cationic surface-active agents or mixtures thereof can be used as surface-active agents. Cationic polymers or a mixture of anionic and amphoteric surface-active agents are particularly preferred. It is preferred that a mixture of anionic and amphoteric surface-active agents be used, such as Disodium Lauroamphodicetate and Sodium Laureth Sulfate (Rewoteric® AM G30) or Plantaren® XLS, Plantaren® TLS, Standapol® AP blend.

Said preferred agents are preferably used in amounts ranging between 1 and 60% by weight, particularly 18 and 50% by weight, especially 20 and 40% by weight.

Numerous anionic surface-active agents can potentially be used here. Non-limiting examples of anionic, foaming surface-active agents include those selected from the group consisting of alkyl sulphates and alkyl ether sulphates, sulphatized monoglycerides, sulphonated olefins, alkyl aryl sulphonates, primary or secondary alkane sulphonates, alkyl sulphosuccinates, acyl taurates, acyl isothionates, alkyl glyceryl ether sulphonates, sulphonate methyl esters, sulphonated fatty acids, alkyl phosphates, acyl glutamates, acyl sarcosinates, alkyl sulphoacetates, acylated peptides, alkyl ether carboxylates, acyl lactylates of anionic surface-active agents containing fluorine and mixtures thereof. Mixtures of anionic surface-active agents can effectively be used in the present invention.

Examples of amphoteric surface-active agents which can be used in the present invention include at least those having an acid group. The latter can be a carboxyl group or a sulpho group. Also included are quaternary nitrogen and, consequently, quaternary amino acids. These should in all cases contain an alkyl group or alkenyl group having 7 to 18 carbon atoms. Suitable amphoteric detergents include simple, coconut-derived betaines and amidobetaines which are a mixture of C12 and C14 alkyl groups, so that at least half of the R1 hydrocarbon chain, preferably three quarters thereof, has 10 to 14 carbon atoms. Preferably, the other two R2 and R3 hydrocarbon chains are methyl. The amphoteric detergent can also be a sulphobetaine. Amphoacetates and diamphoacetates can also occur in the form of zwitterionic and/or amphoteric compounds, which can be used as well. Any amphoteric surface-active agent should in general be contained in an amount approx. ranging between 0.1 and 20% by weight, preferably 5 and 18% by weight, relative to the total composition.

Suitable non-ionic surface-active agents include, but are not limited to, coconut-derived acyl monoethanol amides or acyl diethanol amides, alkyl polysaccharides, lactobionamides, ethylene glycol esters, glycerine monoethers, polyhydroxyamides (glucamides), primary and secondary alcohol ethoxylates, particularly C8-C20 aliphatic alcohols which on average are ethoxylated with 1 to 20 moles ethylene oxide per mole alcohol. Mixtures of the aforesaid surface-active agents can also be used.

Examples of synthetic, quaternized polymers (cationic polymers) include, but are not limited to, Polyquaternium-1, Polyquaternium-2, Polyquaternium-5, Polyquaternium-6, Polyquaternium-7, Polyquaternium-8, Polyquaternium-9, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-39, Polyquaternium-57 and mixtures thereof, the aforesaid compound names being names assigned by the Cosmetic, Toiletry and Fragrance Association and listed in the CTFA International Cosmetic Ingredient Dictionary, J. Nikitakis, ed., Cosmetic, Toiletry and Fragrance Association, Inc., Washington D.C. (1991).

Quaternized polymers derived from natural substances are particularly suitable for the composition and method of the present invention. Examples of quaternized polymers derived from natural substances are, without limitation to their name in "The CTFA International Dictionary", Polyquaternium-4, Polyquaternium-10, Polyquaternium-24, Guar Hydroxypropyltrimonium Chloride, cocodimonium hydroxypropyl hydrolyzed rice protein, stearyldimonium hydroxypropyl hydrolyzed rice protein, hydroxypropyltrimonium hydrolyzed silk, cocodimonium hydroxypropyl soy protein, lauryldimonium hydroxypropyl hydrolyzed soy protein, hydroxypropyltrimonium hydrolyzed soy protein, hydroxypropyltrimonium hydrolyzed vegetable protein, stearyldimonium hydroxypropyl hydrolyzed vegetable protein, cocodimonium hydroxypropyl hydrolyzed wheat protein, stearyldimonium hydroxypropyl hydrolyzed wheat protein and mixtures thereof. In addition, synthetic and natural quaternized polymers can be used in combination with one another.

An especially advantageous quaternized polymer is Guar Hydroxypropyltrimonium Chloride, which is commercially available from Rhone-Poulenc, Cranbury, N.J., under the trade name HI-CARE 1000®. Other guar-based quaternized substances available on the market are JAGUAR C-162, JAGUAR C-138, JAGUAR C-145 and JAGUAR C-17, JAGUAR C-13S from Rhone-Poulenc, Cranbury, N.J. Suitable quaternized cellulose compounds include, but are not limited to, CELQUAT SC-240 (Polyquaternium-10) and CELQUAT L200 (Polyquaternium-4) from the National Starch and Chemical Corp., Bridgewater, N.J., and QUATRISOFT LM-200 (Polyquaternium-24) from the Amerchol Corp., Edison, N.J.

Suitable diblock or triblock copolymers are those based on styrene, ethylene and butylene as well as ethylene, propylene and styrene. These include e.g. those of the KRATON D and KRATON G product lines marketed by the Kraton Chemical Company. KRATON G 1650, a styrene/ethylene-butylene/styrene triblock copolymer, and KRATON G 1702, an ethylene-propylene/styrene diblock copolymer, are particularly preferred. It is possible to use either diblock or triblock copolymers of the aforesaid type, however, in a preferred composition, a mixture of diblock and triblock copolymers in a weight ratio of 2:1 to 1:3 is used. In the context of the present invention, the term "styrene" covers both styrenes and substituted styrenes, such as ortho-, meta-1- and pure alkyl styrenes as well as x-alkyl styrenes, wherein alkyl is a C1-C3 alkyl group.

It is preferred that the saturated liquid oligomer of an unsaturated fatty acid be a dimer or trimer, particularly a dimer of e.g. a C17-C21 fatty acid, for example of linoleic acid, as is e.g. commercially available from Uniqema, such as Pripol 1006, Pripure 1009; and from Cognis, such as Empol 1004, 1007 1008, 1016, etc.

Oils which can be used in the composition according to the invention include vegetable oils, esters, hydrocarbon oils, animal fats, fatty acids and fatty alcohols.

These include vegetable oils, such as peanut oil, castor oil, cocoa butter, coconut oil, maize oil, cotton seed oil, olive oil, palm kernel oil, rapeseed oil, safflower seed oil, sesame seed oil and soybean oil as well as sunflower seed oil.

DETAILED DESCRIPTION OF THE INVENTION

According to the invention, useable esters are Butyl Myristate, Cetyl Palmitate, Decyl Oleate, Glyceryl Laurate, Glyceryl Ricinoleate, Glyceryl Stearate, Glyceryl Isostearate, Hexyl Laurate, Isobutyl Palmitate, Isocetyl Stearate, Isopropyl Isostearate, Isopropyl Laurate, Isopropyl Linoleate, Isopropyl Myristate, Isopropyl Palmitate, Isopropyl Stearate, Propylene Glycol Monolaurate, Propylene Glycol Ricinoleate, Propylene Glycol Stearate and Propylene Glycol Isostearate.

Silicone oils which can be used according to the invention are silicone oils as such, gums and modifications thereof such as linear and cyclic polydimethylsiloxanes; amino, alkyl, alkyl aryl and aryl silicone oils.

Hydrocarbons which can be used according to the invention are those as liquid paraffins, petrolatum, microcrystalline wax, ceresin, squalenes, squalanes and mineral oil.

Animal fats which can be used according to the invention are lanolin alcohols, acylated lanolin alcohols, lanolin, lard, mink oil and tallow.

Fatty acids and alcohols which can be used according to the invention are behenic acid, palmitic acid, lauric acid, myristic acid, oleic acid, linoleic acid, linolenic acid, lanoleic acid, stearic acid, isostearic acid and polyunsaturated fatty acids.

Alcohols include, but are not limited to, lauryl alcohol, behenyl alcohol, cetyl alcohol, stearyl alcohol, oleyl alcohol, eicosanyl alcohol and isocetyl alcohol, cholesterol alcohol and 2-hexadecanol.

It is preferred that oil or fat make up 12 to 25% by weight.

The cleansing composition according to the invention has a very good foaming ability, especially if it contains high proportions of surface-active agents and oils, e.g. if the amount of surface-active agent contained ranges between 5 and 60% by weight and the ratio of surface-active agent to oil is 1:0.6-0.8, particularly 1:0.7-0.78, while the anti-foaming effect which is usually observed in case of such high contents is significantly reduced. This is demonstrated by a foam stability test.

Said foam stability test is carried out as follows: 4 g of a 10% aqueous solution of the product to be tested is mixed with 146 g water having a hardness of 0.5 mmol/l of alkaline earth metal ions (corresponding to a US hardness of 50 ppm) and a temperature of 29° C.+1° C. The test solution is stirred at medium stirring speeds in an Osterizer Blender for 10 seconds. The foam obtained is filled into a graduated 500 ml cylinder and the initial foam volume in mm is determined at the nearest 5 ml graduation. 3.5 minutes later, the height of the foam at the foam/water interface is determined with the same accuracy. The second value in mm represents the foam stability, and the average foam stability is determined by averaging at least three measured values of the same test solution.

The compositions according to the invention have an improved average foam stability ranging between 35 and 60 mm according to the foam stability test.

The water content of the composition according to the invention preferably ranges between 20 and 75% by weight, particularly 25 and 35% by weight.

Further constituents of the composition according to the invention can be lipids, vitamins, UV-filters, phospholipids, electrolytes, antioxidants, protectants, perfumes, pH-adjusters.

Preferred lipids include cholesterol, ceramides, sugar esters and pseudo-ceramides, such as described in EP-A-556 957.

Preferred vitamins include those as vitamins A and E and vitamin alkyl esters, including vitamin C alkyl esters.

Preferred UV-filters are those as Octyl Methoxy Cinnamate (Parsol MCX) and Butyl Methoxy Benzoylmethane (Parsol 1789).

Phospholipids and mixtures of the aforesaid substances are included as well.

Preferred electrolytes are those as sodium chlorides, magnesium sulphate, etc.

A preferred antioxidant is e.g. butylated hydroxytoluene (BHT), advantageously in amounts of approx. 0.01%, or above if desired. Further antioxidants are the vitamins A, C, E and derivatives thereof; flavones or flavonoids; amino acids such as histidine, glycine, tyrosine, tryptophan and derivatives thereof; carotenoids and carotenes such as α-carotene, β-carotene; uric acid and derivatives thereof; α-hydroxy acids such as citric acid, lactic acid, malic acid.

Preferred protectants are antimicrobial agents such as 2-hydroxy-4,2'4'-trichlorodiphenyl ether (DP300) and protectants such as dimethyloldimethylhydantoin (Glydant XL1000), parabenes, sorbic acid, etc.

Suitable pH-adjusters are e.g. citric acid, disodium EDTA, triethanolamine, etc.

The most important advantages of the new composition are the following:

It considerably improves the deposition of skin-conditioning emollients and enhances the long-lasting moisturizing of the skin once it has been rinsed off.

If high proportions of surface-active agent and oil are contained, it has a very good foaming ability and is an ultra-mild body wash without phase separation.

It overcomes the tendency that no foam will form if high proportions of surface-active agent and oil are contained.

It enables a super-stable emulsion to be produced.

The cleansing composition according to the invention has a viscosity ranging between 100 and 600 mPa·s (cP) necessary for use on wet skin in a shower and can be rinsed off easily at the same time. Once the act of bathing or showering is finished, the composition has a long-lasting skin-conditioning effect without feeling oily. It surpasses the products currently available on the market, especially due to its foaming ability and moisturizing properties. In addition, the same cleansing effect is achieved using milder surface-active agents.

The cosmetic composition according to the invention can e.g. be used in the form of washing lotions, deep-action hair care products, hair conditioners, hair shampoos, shower gels, shower lotions, bath oils, cleansing creams, pasty masks (mud packs).

The aforesaid products can be manufactured in a manner known to those skilled in the art.

The invention will now be explained in more detail by means of examples. All quantities are in % by weight unless indicated otherwise.

EXAMPLE 1

Moisturizing Body Wash I

| | |
|---|---|
| Water | q.s. ad 100 |
| Sodium Laureth Sulfate (70%) | 20.8 |
| Sunflower Oil | 14 |
| Sodium Lauroamphoacetate (30%) | 16.6 |
| Glycerine | 4 |
| Petrolatum | 3 |
| Dimer Acid Hydrogenated (Pripol 1006) | 2 |
| Petrolatum with E/P/S Copolymer (Versagel P200) | 1 |
| Cocoamide MEA | 1.5 |
| Perfume Oil | 1 |
| Guar Hydroxypropyltrimonium Chloride | 0.3 |
| Citric Acid | as required for pH 5.5 |
| DMDM Hydantoin | 0.2 |
| Tetrasodium EDTA | 0.05 |

EXAMPLE 2

Moisturizing Body Wash II

| | |
|---|---|
| Water | q.s. ad 100 |
| Sodium Laureth Sulfate (70%) | 20.8 |
| Sunflower Oil | 14 |
| Sodium Lauroamphoacetate (30%) | 16.6 |
| Glycerine | 4 |
| Dimer Acid Hydrogenated (Pripol 1006) | 2.5 |
| Petrolatum with E/P/S Copolymer (Versagel P200) | 1 |
| Cocoamide MEA | 1.5 |
| Perfume Oil | 1 |
| Guar Hydroxypropyltrimonium Chloride | 0.3 |
| Citric Acid | as required for pH 5.5 |
| DMDM Hydantoin | 0.2 |
| Tetrasodium EDTA | 0.05 |

EXAMPLE 3

Moisturizing Body Wash III

| | |
|---|---|
| Water | q.s. ad 100 |
| Sodium Laureth Sulfate (70%) | 20.8 |
| Sonnenblumenöl | 14 |
| Sodium Lauroamphoacetate (30%) | 16.6 |
| Glycerine | 4 |
| Dimer Acid Hydrogenated (Pripol 1006) | 1.5 |
| Petrolatum with E/P/S Copolymer (Versagel P200) | 1 |
| Cocoamide MEA | 1.5 |
| Perfume Oil | 1 |
| Guar Hydroxypropyltrimonium Chloride | 0.3 |
| Citric Acid | as required for pH 5.5 |
| DMDM Hydantoin | 0.2 |
| Tetrasodium EDTA | 0.05 |

EXAMPLE 4

Moisturizing Body Wash IV

| | |
|---|---|
| Water | q.s. ad 100 |
| Sodium Laureth Sulfate (70%) | 20.8 |
| Sunflower Oil | 18 |
| Sodium Lauroamphoacetate (30%) | 16.6 |
| Glycerine | 4 |
| Dimer Acid Hydrogenated (Pripol 1006) | 1.0 |
| Petrolatum with E/P/S Copolymer (Versagel P200) | 1 |
| Cocoamide MEA | 1.5 |
| Perfume Oil | 1 |
| Guar Hydroxypropyltrimonium Chloride | 0.3 |
| Citric Acid | as required for pH 5.5 |
| DMDM Hydantoin | 0.2 |
| Tetrasodium EDTA | 0.05 |

EXAMPLE 5

Moisturizing Body Wash V

| | |
|---|---|
| Water | q.s. ad 100 |
| Sodium Laureth Sulfate (70%) | 20.8 |
| Sunflower Oil | 18 |
| Disodium Lauroamphoacetate (30%) | 16.6 |
| Glycerine | 4 |
| Dimer Acid Hydrogenated (Pripol 1006) | 2.0 |
| Petrolatum with E/P/S Copolymer (Versagel P200) | 1 |

-continued

| | |
|---|---|
| Cocoamide MEA | 1.5 |
| Perfume Oil | 1 |
| Guar Hydroxypropyltrimonium Chloride | 0.3 |
| Citric Acid | as required for pH 5.5 |
| DMDM Hydantoin | 0.2 |
| Tetrasodium EDTA | 0.05 |

EXAMPLE 6

Moisturizing Body Wash VI

| | |
|---|---|
| Water | q.s. ad 100 |
| Sodium Laureth Sulfate (70%) | 20.8 |
| Sunflower Oil | 18 |
| Sodium Lauroamphoacetate (30%) | 16.6 |
| Glycerine | 4 |
| Dimer Acid Hydrogenated (Pripol 1006) | 1.5 |
| Petrolatum with E/P/S Copolymer (Versagel P200) | 1 |
| PPG-2 Hydroxyethyl Coco/Isostearamide | 1.5 |
| Perfume Oil | 1 |
| Guar Hydroxypropyltrimonium Chloride | 0.3 |
| Citric Acid | as required for pH 5.5 |
| DMDM Hydantoin | 0.2 |
| Tetrasodium EDTA | 0.05 |

EXAMPLE 7

Moisturizing Body Wash VII

| | |
|---|---|
| Water | q.s. ad 100 |
| Sodium Laureth Sulfate (70%) | 20.8 |
| Sunflower Oil | 18 |
| Disodium Lauroamphoacetate (30%) | 16.6 |
| Glycerine | 4 |
| Dimer Acid Hydrogenated (Pripol 1006) | 1.5 |
| Petrolatum with E/P/S Copolymer (Versagel P200) | 1 |
| PPG-2 Hydroxyethyl Coco/Isostearamide | 1.5 |
| Perfume Oil | 1 |
| Guar Hydroxypropyltrimonium Chloride | 0.3 |
| Citric Acid | as required for pH 5.5 |
| DMDM Hydantoin | 0.2 |
| Tetrasodium EDTA | 0.05 |

EXAMPLE 8

Comparative Example

The foam height was determined according to the foam stability test described above. The results are shown in the following Table 1.

TABLE 1

| Sample | Initial foam height (mm) | Average (mm) | Final foam height (mm) | Average (mm) |
|---|---|---|---|---|
| G-221D$_1$ | 35 | 53.3 | 25 | 38.3 |
| G-221D$_2$ | 75 | | 50 | |
| G-221D$_3$ | 50 | | 40 | |
| G-221E$_1$ | 45 | 63.3 | 40 | 53.3 |
| G-221E$_2$ | 85 | | 80 | |
| G-221E$_3$ | 60 | | 40 | |
| G-221F$_1$ | 100 | 65 | 60 | 43.3 |
| G-221F$_2$ | 65 | | 50 | |
| G-221F$_3$ | 30 | | 20 | |
| G-221 with DA1 | 80 | 75 | 70 | 65 |
| G-221 with DA2 | 75 | | 65 | |
| G-221 with DA3 | 70 | | 60 | |
| G-221 without DA1 | 75 | 85 | 65 | 75 |
| G-221 without DA2 | 90 | | 80 | |
| G-221 without DA3 | 90 | | 80 | |
| CA1 | 15 | 15 | 5 | 3.3 |
| CA2 | 15 | | 5 | |
| CA3 | 15 | | 0 | |
| CB1 | 25 | 30 | 15 | 16.7 |
| CB2 | 35 | | 20 | |
| CB3 | 30 | | 15 | |

Explanatory notes:
G-221D = Body wash according to Example 1 containing 2.5% Dimer Acid Hydrogenated (hereinafter referred to as Dimer)
G-221E = Body wash according to Example 1 containing 2.0% Dimer
G-221F = Body wash according to Example 1 containing 1.5% Dimer
G-221 with DA = Body wash according to Example 1 containing 1.0% Dimer and oil
G-221 without DA = Body wash according to Example 1 containing oil, but no Dimer
CA = Product marketed by a competitor
CB = Product marketed by another competitor The compositions of the present invention have a considerably improved foam height compared to products of the same category which are currently available on the market. The foam height decreased slightly when the amount of Dimer Acid Hydrogenated contained was increased, but it was still higher than that of the market products even at a Dimer content of 2.5%. As an additional check, a sample containing no Dimer was tested, whose foam height was considerably higher too. All in all, this shows a clear superiority of the products according to the invention in case of high contents of surface-active agents and oil.

We claim:

1. A liquid cosmetic cleansing composition comprising
5 to 60% by weight of a surface-active agent;
0.1 to 10% by weight of a diblock or triblock copolymer or a mixture thereof;
0.1 to 5% by weight of a saturated liquid oligomer of an unsaturated fatty acid, said oligomer having more than 30 carbon atoms;
0.1 to 30% by weight of an oil or fat;
10 to 80% by weight of water,
all of the above percentages being relative to the total weight of the composition,
which cleansing composition has an improved average foam stability ranging between 35 and 60 mm according to the foam stability test, wherein the ratio of surface-active agent to oil is in the range of 1:0.6-1:0.8.

2. A cleansing composition according to claim 1, wherein said saturated liquid oligomer of an unsaturated fatty acid is a dimer of a C17-C21 fatty acid.

3. A cleansing composition according to claim 2, wherein said saturated liquid oligomer of an unsaturated fatty acid is a dimer of linoleic acid.

4. A cleansing composition according to claim 1, wherein the surface-active agent comprises 18-50% by weight of the composition.

5. A cleansing composition according to claim 1, wherein the surface-active agent comprises 20-40% by weight of the composition.

6. A cleansing composition according to claim 1, wherein the oil or fat comprises 12-25% by weight of the composition.

7. A cleansing composition according to claim 1, wherein said diblock or triblock copolymer comprises styrene, ethylene, butylene, or a combination thereof.

8. A liquid cosmetic cleansing composition comprising 18 to 50% by weight of a surface-active agent;

0.1 to 10% by weight of a diblock or triblock copolymer or a mixture thereof;

0.1 to 5% by weight of a saturated liquid oligomer of an unsaturated fatty acid, wherein said saturated liquid oligomer of an unsaturated fatty acid is a dimer of a C17-C21 fatty acid;

12 to 25% by weight of an oil or fat;

10 to 80% by weight of water, all of the above percentages being relative to the total weight of the composition, which cleansing composition has an improved average foam stability ranging between 35 and 60 mm according to the foam stability test, wherein the ratio of surface-active agent to oil is in the range of 1:0.6-1:0.8.

9. A cleansing composition according to claim 8, wherein said composition contains a cationic surface-active agent.

10. A cleansing composition according to claim 8, wherein said composition contains a mixture of an anionic surface-active agent and an amphoteric surface-active agent.

11. A cleansing composition according to claim 8, wherein said diblock or triblock copolymer is a styrene/ethylene-butylene/styrene copolymer or an ethylene-propylene/styrene copolymer or a mixture thereof.

12. A cleansing composition according to claim 8, wherein the ratio of surface-active agent to oil is in the range of 1:0.7-0.8.

13. A cleansing composition according to claim 8, wherein said diblock or triblock copolymer comprises styrene, ethylene, butylene, or a combination thereof.

* * * * *